(12) United States Patent
Hwang et al.

(10) Patent No.: US 11,179,319 B2
(45) Date of Patent: Nov. 23, 2021

(54) METHOD FOR PRODUCING COSMETIC COMPOSITION USING SKIN SERUM

(71) Applicant: AMOREPACIFIC CORPORATION, Seoul (KR)

(72) Inventors: Joonyoung Hwang, Yongsin-si (KR); Kyeonghwan Hwang, Yongsin-si (KR); Jin Seob Shin, Yongsin-si (KR); Eun-Soo Lee, Yongsin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 107 days.

(21) Appl. No.: 16/479,052

(22) PCT Filed: Jan. 31, 2018

(86) PCT No.: PCT/KR2018/001310
§ 371 (c)(1),
(2) Date: Jul. 18, 2019

(87) PCT Pub. No.: WO2018/155829
PCT Pub. Date: Aug. 30, 2018

(65) Prior Publication Data
US 2019/0365638 A1 Dec. 5, 2019

(30) Foreign Application Priority Data

Feb. 24, 2017 (KR) .................. 10-2017-0024898

(51) Int. Cl.
*A61K 36/00* (2006.01)
*A61K 8/9789* (2017.01)
*A61K 8/34* (2006.01)
*A61K 8/49* (2006.01)
*A61Q 19/00* (2006.01)

(52) U.S. Cl.
CPC ............ *A61K 8/9789* (2017.08); *A61K 8/345* (2013.01); *A61K 8/498* (2013.01); *A61Q 19/00* (2013.01); *A61K 2800/82* (2013.01); *A61K 2800/85* (2013.01)

(58) Field of Classification Search
None
See application file for complete search history.

(56) References Cited

U.S. PATENT DOCUMENTS

| 8,685,475 B2 | 4/2014 | Kwack et al. | |
|---|---|---|---|
| 2005/0118215 A1* | 6/2005 | Anderson | A61Q 19/00 424/401 |
| 2008/0103103 A1* | 5/2008 | Memarzadeh | A61K 31/353 514/27 |
| 2011/0117220 A1 | 5/2011 | Kang et al. | |
| 2014/0004210 A1* | 1/2014 | Iino | A61Q 19/007 424/725 |

FOREIGN PATENT DOCUMENTS

| JP | 2001172160 A | * | 6/2001 |
|---|---|---|---|
| JP | 2003204787 A | * | 7/2003 |
| KR | 1020050013352 A | | 2/2005 |
| KR | 1020110053051 A | | 5/2011 |
| KR | 1020160015705 A | | 2/2016 |
| KR | 1020160103756 A | | 9/2016 |
| KR | 101684664 B1 | | 12/2016 |
| KR | 1020160146136 A | | 12/2016 |

OTHER PUBLICATIONS

Phromrukachat, Assessment of active ingredients in pickled tea. Asian Journal of Food and Agro-Industry (2010), vol. 3, No. 3, pp. 312-318 (Year: 2010).*
Shin, Evaluation of the antiviral activity of a green tea solution as a hand-wash disinfectant. Bioscience, biotechnology, and biochemistry, (2012) vol. 76, No. 3, pp. 581-4 (Year: 2012).*
International Search Report for International Application No. PCT/KR2018/001310, International Filing Date Jan. 31, 2018, dated May 8, 2018, 4 pages.

* cited by examiner

*Primary Examiner* — Qiuwen Mi
(74) *Attorney, Agent, or Firm* — Cantor Colburn LLP (57) ABSTRACT

The present specification relates to a method for extracting a plant by using a skin serum that can be used for skin care. This method can further increase the process efficiency and extract active ingredients more effectively than conventional extraction methods using a solvent. Thus, the method can increase customer satisfaction and promote the development of relevant industries.

14 Claims, 8 Drawing Sheets

METHOD FOR PRODUCING COSMETIC COMPOSITION USING SKIN SERUM

This application is a national stage application of PCT/KR2018/001310, filed Jan. 31, 2018, which claims the benefit of and priority to KR 10-2017-0024898, filed Feb. 24, 2017 both of which are hereby incorporated by reference in their entirety.

TECHNICAL FIELD

The present invention relates to a preparing method of a cosmetic composition using a skin cosmetic solution and an extraction solvent consisting of a skin cosmetic solution and which is for use in plant extraction in the preparation of a cosmetic composition containing a plant extract. Also, the present invention relates to an extract and a cosmetic composition using the same.

BACKGROUND ART

Extraction is a process of dissolving and separating only a specific ingredient from a solid or liquid mixture by mainly using a liquid solvent. It is a separation method which is important not only in chemical and biological experiments but also industrially. It may use a chemical reaction such as an acid-base reaction or a chelate formation reaction, or merely a difference in solubility. Extraction from a solid is called solid-liquid extraction, and extraction from a liquid is called liquid-liquid extraction. The solid-liquid extraction is sometimes referred to as leaching.

Among extractions, the solvent extraction refers to dissolving and separating one type (sometimes two or more types) of ingredient from a solid or liquid sample using a solvent. In the chemical analysis or use of a mixture, there is a case where an ingredient of a test material well dissolves in a particular solvent while the other ingredients thereof do not dissolve in the solvent.

Extraction solvent refers to a liquid solvent used to dissolve and separate a specific material from a solid mixture or a liquid mixture. It includes water, alcohol, ether, petroleum ether, benzene, ethyl acetate, chloroform, mercury, etc. In recent years, extraction methods using a supercritical fluid (SCF) as a solvent are also widely used.

As described above, extraction may be performed using only a solvent. However, extraction may also be performed by a chemical reaction such as an acid-base reaction or chelate formation in a mixture. A Soxhlet extractor is used to extract a solid mixture using a solvent and a separatory funnel is used to extract a liquid mixture.

In order to extract or separate an ingredient from a plant, it is usually most preferable to use a plant immediately after collecting it. The most often used method is immersing a plant in hot water, hot methanol or hot ethanol immediately after collection. A plant may be dried before extracting an ingredient therefrom. In this case, care should be taken so that the ingredients in the plant tissue during will not change during drying. Thus, it is advisable to dry a plant material at a low temperature or in a well-ventilated place as soon as possible. Once a plant material is dried, even long-term preservation thereof does not greatly interfere with the studies of its ingredients. In fact, components of vegetable matter such as flavonoids, alkaloids, and terpenoids may not change significantly even after years of drying.

There is an increasing consumer demand for products containing a plant extract, particularly for the preparation of cosmetics. Therefore, studies are being conducted on effective and safe extraction methods and extraction solvents.

CITATION LIST

Patent Literature

[Patent Literature 1]
   Korean Patent Application No. 10-2009-0114513

SUMMARY OF INVENTION

Technical Problem

In one aspect, the object of the present invention is to provide an effective and safe extraction solvent, an extraction method using the same, and a cosmetic composition using the same.

Solution to Problem

In order to achieve the above object, the present invention provides a preparing method of a cosmetic composition containing a plant extract, comprising the steps of: extracting an extract from a plant using a skin cosmetic solution; and adding an additional ingredient to the extract extracted at the above step to prepare a cosmetic composition.

Further, the present invention provides an extraction solvent consisting of a skin cosmetic solution, which is for use in plant extraction in the preparation of a cosmetic composition containing a plant extract.

Further, the present invention provides an extract comprising the extraction solvent and an ingredient extracted thereby from a plant.

Further, the present invention provides a cosmetic composition comprising the extract.

Advantageous Effects of Invention

The preparing method according to one aspect of the present invention allows to further increase the efficiency of the process than the extraction methods using a conventional solvent.

The cosmetic composition comprising an extract extracted using an extraction solvent according to one aspect of the present invention has a high active ingredient content extracted and is excellent in the effect on the skin.

DESCRIPTION OF EMBODIMENTS

As used herein, the term "skin cosmetic solution" refers to a fluid composition that can be applied to the skin for various cosmetic purposes. It mainly includes liquid or essence formulations such as a softening lotion, a nourishing lotion and a milky lotion. It may also include an emulsion, a solubilizer, a moisturizer, water, and other chemicals.

As used herein, the term "extract" includes all materials obtained by extracting an ingredient of a natural product, regardless of the extraction method, extraction solvent, extracted ingredient or the form of extract. It also covers all materials that can be obtained by processing or treating a material obtained by extracting an ingredient of a natural product, using another method. Specifically, the processing or treatment may be an additional fermentation or enzymatic treatment of an extract. Thus, the extract as used herein covers a fermentation product, a concentrate, and a dried product.

As used herein, the term "glycerin derivative" refers to a compound obtained by chemically changing a part of glycerin and which is similar to glycerin. It means a compound obtained by substituting a hydrogen atom or a specific atomic group in glycerin with another atom or atomic group.

Conventional cosmetic compositions comprising a plant extract are prepared by extracting a plant using a widely used general extraction method, reducing the resultant and introducing the thus obtained product into a cosmetic composition. In general extraction methods, extraction is performed using an organic solvent, water or a mixture thereof as a solvent, the solvent is removed by evaporation of the solvent from the extracted liquid phase, and then the resultant is reprocessed into a form that can be used for cosmetics, which is then used for cosmetics. The extraction methods using a general solvent are effective in terms of cost and time. However, they may have disadvantages that among the various ingredients of the raw material, only those which have solubility in a specific solvent are partially extracted or that an ingredient may be lost during the evaporation or additional processing after extraction. In addition, there is a possibility that a small amount of the used organic solvent may remain, resulting in adverse effects to the skin.

In one aspect, the present invention relates to a method for extracting plants directly using a combination of raw materials that can be used as a skin cosmetic solution. This method can prevent the loss of extracted ingredients because it does not require an additional treatment process such as solvent removal. Also, it does not have the toxic properties of conventional solvents. Thus, the present invention can overcome all of the disadvantages as mentioned above.

In one aspect, the present invention relates to a preparing method of a cosmetic composition containing a plant extract, comprising the steps of: extracting an extract from a plant using a skin cosmetic solution; and adding an additional ingredient to the extract extracted at the above step to prepare a cosmetic composition. There is no known process for obtaining an extract from a plant using a skin cosmetic solution itself. One aspect of the present invention includes the new constitution and thereby achieves the above effects.

In one embodiment, the plant may be any plant that can be subjected to the extraction using a skin cosmetic solution and may be any part such as a leaf, a stem, a fruit, a flower, and a root. However, preferably, the plant may be a tea leaf.

In another embodiment, the plant may be a fermented tea leaf. The fermentation may include both natural fermentation and fermentation by microbial inoculation. However, preferably, the fermentation may be natural fermentation.

In another embodiment, the extraction may be, but not limited to, ultrasonic extraction, room temperature extraction, cold extraction, or reflux cooling extraction.

In another embodiment, the extraction may be performed at 10 to 50° C. For example, the extraction may be performed at 10° C. or higher, 20° C. or higher, 25° C. or higher, 30° C. or higher, 40° C. or higher, or 45° C. or higher. Also, the extraction may be performed at 50° C. or lower, 45° C. or lower, 40° C. or lower, 30° C. or lower, 25° C. or lower, 20° C. or lower, or 15° C. or lower.

In another embodiment, the extraction may be performed for 3 to 30 hours. For example, the extraction time may be 3 hours or more, 5 hours or more, 8 hours or more, 10 hours or more, 12 hours or more, 14 hours or more, 16 hours or more, 18 hours or more, 20 hours or more, 25 hours or more, or 28 hours or more. Also, the extraction time may be 30 hours or less, 25 hours or less, 20 hours or less, 18 hours or less, 16 hours or less, 14 hours or less, 12 hours or less, 10 hours or less, 8 hours or less, or 5 hours or less.

In another embodiment, the extraction may be performed at 5 to 100 rpm. For example, the rpm may be 5 or more, 7 or more, 9 or more, 10 or more, 12 or more, 15 or more, 20 or more, 30 or more, 40 or more, 50 or more, 60 or more, 70 or more, 80 or more, or 90 or more. Also, the rpm may be 100 or less, 90 or less, 80 or less, 70 or less, 60 or less, 50 or less, 40 or less, 30 or less, 20 or less, 15 or less, 12 or less, 10 or less, 9 or less, or 7 or less.

According to another aspect of the present invention, the extraction step may further comprise a filtering step. In one embodiment, the filtering may be filtration, more preferably, filtration after centrifugation.

In another aspect, the present invention may relate to an extraction solvent consisting of a skin cosmetic solution, which is for use in plant extraction in the preparation of a cosmetic composition containing a plant extract.

In one embodiment, the skin cosmetic solution may comprise one or more selected from the group consisting of a $C_2$ to $C_{20}$ dihydric alcohol and a $C_2$ to $C_{20}$ trihydric alcohol.

In another embodiment, the dihydric alcohol may be one or more selected from the group consisting of butylene glycol, propanediol, and hexanediol. Also, the trihydric alcohol may be one or more of glycerin and a glycerin derivative.

In another embodiment, the butylene glycol may be 1,3-butylene glycol, the propanediol may be 1,3-propanediol, and the hexanediol may be 1,2-hexanediol.

In another embodiment, the glycerin derivative may be ethylhexyl glycerin.

In another embodiment, the skin cosmetic solution may comprise glycerin, butylene glycol, propanediol, hexanediol, and ethylhexyl glycerin.

In one embodiment, the content of the butylene glycol may be 10 to 25% by weight based on the total weight of the extraction solvent. If the content exceeds 25% by weight, it is not possible to use it due to the increase of viscosity, the impossibility of filtration, etc. If the content is less than 10% by weight, the extraction effect significantly decreases. In one aspect, the content of the butylene glycol may be 10% by weight or more, 12% by weight or more, 14% by weight or more, 16% by weight or more, 18% by weight or more, 20% by weight or more, 22% by weight or more, or 24% by weight or more based on the total weight of the extraction solvent. Also, the content may be 25% by weight or less, 22% by weight or less, 20% by weight or less, 18% by weight or less, 16% by weight or less, 14% by weight or less, or 12% by weight or less.

In another embodiment, the content of the propanediol may be 1 to 20% by weight based on the total weight of the extraction solvent. If the content exceeds 20% by weight, it is not possible to use it due to the increase of viscosity, the impossibility of filtration, etc. If the content is less than 1% by weight, the extraction effect significantly decreases. In one aspect, the content may be 1% by weight or more, 4% by weight or more, 6% by weight or more, 8% by weight or more, 10% by weight or more, 12% by weight or more, 14% by weight or more, 16% by weight or more, or 18% by weight or more. Also, the content may be 20% by weight or less, 18% by weight or less, 16% by weight or less, 14% by weight or less, 12% by weight or less, 10% by weight or less, 8% by weight or less, 6% by weight or less, 4% by weight or less, or 2% by weight or less.

In another embodiment, the content of the hexanediol may be 0.1 to 5% by weight based on the total weight of the extraction solvent. If the content exceeds 5% by weight, it is not possible to use it due to the increase of viscosity, the impossibility of filtration, etc. If the content is less than 0.1% by weight, the extraction effect significantly decreases. In one aspect, the content may be 0.1% by weight or more, 0.4% by weight or more, 0.6% by weight or more, 0.8% by weight or more, 1% by weight or more, 1.2% by weight or more, 1.5% by weight or more, 2% by weight or more, 2.5% by weight or more, 3% by weight or more, 3.5% by weight or more, 4% by weight or more, or 4.5% by weight or more. Also, the content may be 5% by weight or less, 4.5% by weight or less, 4% by weight or less, 3.5% by weight or less, 3% by weight or less, 2.5% by weight or less, 2% by weight or less, 1.5% by weight or less, 1.2% by weight or less, 1% by weight or less, 0.8% by weight or less, 0.6% by weight or less, 0.4% by weight or less, or 0.2% by weight or less.

In another embodiment, the content of the glycerin may be 5 to 20% by weight based on the total weight of the extraction solvent. If the content exceeds 20% by weight, it is not possible to use it due to the increase of viscosity, the impossibility of filtration, etc. If the content is less than 5% by weight, the extraction effect significantly decreases. In one aspect, the content may be 5% by weight or more, 7% by weight or more, 9% by weight or more, 11% by weight or more, 13% by weight or more, 15% by weight or more, 17% by weight or more, or 19% by weight or more. Also, the content may be 20% by weight or less, 18% by weight or less, 16% by weight or less, 14% by weight or less, 12% by weight or less, 10% by weight or less, 8% by weight or less, or 6% by weight or less.

In another embodiment, the content of the glycerin derivative may be 0.01 to 10% by weight based on the total weight of the extraction solvent. If the content exceeds 10% by weight, it is not possible to use it due to the increase of viscosity, the impossibility of filtration, etc. If the content is less than 0.01% by weight, the extraction effect significantly decreases. In one aspect, the content may be 0.01% by weight or more, 0.05% by weight or more, 0.08% by weight or more, 0.1% by weight or more, 0.12% by weight or more, 0.14% by weight or more, 0.2% by weight or more, 0.4% by weight or more, 0.6% by weight or more, 0.8% by weight or more, 1% by weight or more, 4% by weight or more, 6% by weight or more, or 8% by weight or more. Also, the content may be 8% by weight or less, 6% by weight or less, 4% by weight or less, 1% by weight or less, 0.8% by weight or less, 0.6% by weight or less, 0.4% by weight or less, 0.2% by weight or less, 0.14% by weight or less, 0.12% by weight or less, 0.1% by weight or less, 0.08% by weight or less, 0.05% by weight or less, or 0.02% by weight or less.

According to one aspect of the present invention, the weight ratio of the glycerin: the butylene glycol may be 1:0.5 to 5. In one aspect, the ratio may be 1:0.5 or more, 1:0.7 or more, 1:0.9 or more, 1:1.0 or more, 1:1.2 or more, 1:1.4 or more, 1:1.6 or more, 1:1.8 or more, 1:2 or more, 1:2.5 or more, 1:2.8 or more, 1:3 or more, 1:3.5 or more, 1:4 or more, or 1:4.5 or more. Also, the ratio may be 1:5 or less, 1:4.5 or less, 1:4 or less, 1:3.5 or less, 1:3 or less, 1:2.5 or less, 1:2 or less, 1:1.5 or less, 1:1.2 or less, 1:1 or less, 1:0.8 or less, or 1:0.6 or less.

In one embodiment, the weight ratio of the butylene glycol: the propanediol may be 1:0.04 to 2. In one aspect, the ratio may be 1:0.04 or more, 1:0.06 or more, 1:0.08 or more, 1:0.1 or more, 1:0.2 or more, 1:0.4 or more, 1:0.6 or more, 1:0.8 or more, 1:1 or more, 1:1.2 or more, 1:1.4 or more, 1:1.6 or more, or 1:1.8 or more. Also, the ratio may be 1:2 or less, 1:1.8 or less, 1:1.6 or less, 1:1.4 or less, 1:1.2 or less, 1:1 or less, 1:0.8 or less, 1:0.6 or less, 1:0.4 or less, 1:0.2 or less, 1:0.1 or less, 1:0.08 or less, or 1:0.06 or less.

In another embodiment, the weight ratio of the propanediol: the hexanediol may be 1:0.005 to 5. In one aspect, the ratio may be 1:0.005 or more, 1:0.01 or more, 1:0.05 or more, 1:0.1 or more, 1:0.5 or more, 1:1 or more, 1:2 or more, 1:3 or more, or 1:4 or more. Also, the ratio may be 1:5 or less, 1:4 or less, 1:3 or less, 1:2 or less, 1:1 or less, 1:0.5 or less, 1:0.1 or less, 1:0.05 or less, 1:0.01 or less, or 1:0.008 or less.

In another embodiment, the weight ratio of the hexanediol: the glycerin derivative may be 1:0.002 to 100. In one aspect, the ratio may be 1:0.002 or more, 1:0.005 or more, 1:0.01 or more, 1:0.05 or more, 1:0.1 or more, 1:0.5 or more, 1:1 or more, 1:5 or more, 1:10 or more, 1:20 or more, 1:30 or more, 1:40 or more, 1:50 or more, or 1:80 or more. Also, the ratio may be 1:100 or less, 1:80 or less, 1:60 or less, 1:40 or less, 1:30 or less, 1:20 or less, 1:10 or less, 1:5 or less, 1:1 or less, 1:0.5 or less, 1:0.1 or less, 1:0.05 or less, 1:0.01 or less, or 1:0.005 or less.

In another aspect, the present invention may relate to an extract comprising the extraction solvent and an ingredient extracted thereby from a plant.

In one embodiment, the extract may be an extract in which the content of epigallocatechin gallate (EGCG) is 20 to 60 mg relative to 1 g of the plant to be extracted (or 100 g of an extract comprising the extraction solvent (or the skin cosmetic solution) and an ingredient extracted thereby from a plant). In one aspect, the content of EGCG may be 20 mg or more, 25 mg or more, 30 mg or more, 35 mg or more, 40 mg or more, 45 mg or more, 50 mg or more, or 55 mg or more. Also, the content may be 60 mg or less, 55 mg or less, 50 mg or less, 45 mg or less, 40 mg or less, 35 mg or less, 30 mg or less, or 25 mg or less.

In another aspect, the present invention may relate to a cosmetic composition comprising the extract.

In another aspect, the present invention may relate to the use of an extraction solvent consisting of the skin cosmetic solution and which is for use in plant extraction in the preparation of a cosmetic composition containing a plant extract.

In another aspect, the present invention may relate to a preparing method of a plant extract, comprising the step of: extracting an extract from a plant using an extraction solvent consisting of the skin cosmetic solution.

In another aspect, the present invention may relate to a cosmetic composition for skin roughness reduction, skin moisturizing, skin elasticity enhancement, skin transparency improvement, antioxidation of the skin, anti-inflammation of the skin or anti-aging of the skin comprising the extract.

In another aspect, the present invention may relate to the use of an extract comprising an ingredient extracted from a plant by an extraction solvent consisting of the skin cosmetic solution, for the preparation of a cosmetic composition for skin roughness reduction, skin moisturizing, skin elasticity enhancement, skin transparency improvement, antioxidation of the skin, anti-inflammation of the skin or anti-aging of the skin.

In another aspect, the present invention may relate to the use of an extract comprising an ingredient extracted from a plant by an extraction solvent consisting of the skin cosmetic solution, for the use for skin roughness reduction, skin moisturizing, skin elasticity enhancement, skin transparency improvement, antioxidation of the skin, anti-inflammation of the skin or anti-aging of the skin.

In another aspect, the present invention may relate to a method for skin roughness reduction, skin moisturizing, skin elasticity enhancement, skin transparency improvement, antioxidation of the skin, anti-inflammation of the skin or anti-aging of the skin, comprising the step of administering a cosmetic composition comprising the plant extract to a subject in need thereof.

Hereinafter, the constitution and effects of one aspect of the present invention will be described in more detail through Preparation Example, Examples, and Test Examples. However, the following examples are provided for illustrative purposes only to facilitate understanding of the present invention, and the scope of the present invention are not limited thereto.

Preparation Example

Preparation of Fermented Green Tea

Fermented green tea was prepared to carry out one embodiment of the present invention.

Specifically, green tea leaves were harvested in the same manner as the ordinary method for harvesting green tea leaves, and natural fermentation was performed for 50 days without a separate microbial inoculation. Fermentation conditions were 45±5° C. and a humidity of 30%. Then, the fermented green tea leaves were aged for 50 days.

EXAMPLES

Preparation of Skin Cosmetic Solution (Extraction Solvent)

In order to prepare a skin cosmetic solution that can be used as an extraction solvent, the conditions of the ingredients that can constitute the solvent were considered first. First, the ingredients were limited to those that can be applied to the skin and to those that can constitute composition that can be used as cosmetics. Also, ingredients were selected which are safe for living organisms and which can extract a sufficient amount of a useful ingredient during extraction. Further, ingredients were selected which can be used for any plant as a raw material (raw material to be extracted), regardless of the part of the plant (leaf, stem, root, flower, fruit, etc.). Experiments were conducted on green tea as one embodiment. However, it was confirmed that any plant that can be extracted with the extraction solvent of the present invention can be used as a raw material to be extracted, regardless of the part of the plant.

The skin safety of the ingredients of the solvent was confirmed by a patch test.

Specifically, a closed patch test (on the back) for each ingredient was conducted on 32 healthy adult females with an average age of 36.36 (those with psoriasis, acne, eczema, or other skin diseases, those who are pregnant or lactating, and those taking contraceptives, antihistamines, etc. were excluded before the test). After 24 hours of application, they were observed for 24 hours. Skin reactions were evaluated according to Frosch & Kligman and CTFA guidelines.

Candidate materials found to meet the above requirements were purified water, glycerin, 1,3-butylene glycol, 1,3-propanediol, 1,2-hexanediol, ethylhexyl glycerin, D-glucose, and betaine. These materials were combined at an appropriate weight and ratio to prepare an extraction solvent.

Also, ethanol, ethyl acetate, and hexane, which are solvents commonly used for general extraction methods, were selected as comparative ingredients.

The extraction method for comparing the extraction efficiency was as follows:

Specifically, the fermented green tea leaves according to the Preparation Example were dried to prepare powders (0.001 to 5% by weight). Then, the powders were mixed with a skin cosmetic solution (5 to 75% by weight) obtained by combining the candidate materials whose safety was confirmed, followed by mixing with purified water (20 to 94.999% by weight). Then, extraction was performed with agitation mixing at 10° C. to 50° C. (particularly, 25° C. is preferable, but the overall experiment was performed in this temperature range) and 5 to 100 rpm (particularly, 10 rpm is preferable, but the overall experiment was performed in this rpm range) for 3 to 20 hours (particularly, 12 hours is preferable, but the overall experiment was performed in this time range). The resultant was then filtered (sequential filtering with a 300 mesh filter (made of nylon), a 3 micrometer filter (porous filter paper) and a 0.45 micrometer filter (porous filter paper)) to prepare an extract. The extracts obtained by the combinations of the candidate materials were analyzed as follows:

The extraction yield of EGCG, a representative ingredient of green tea, was compared by HPLC analysis (mobile phase A:B=7:3, A: 0.5% formic acid in water, B: 0.5% formic acid in methanol, 1.0 ml/min, analytical column: Phenomenex Gemini 5u C18 110A (4.6×150 mm, 5 um), room temperature, detection at 280 nm). Other ingredients were also evaluated and their yields were similar to that of EGCG. EGCG is only an exemplary material to confirm the extraction efficiency.

The results showed that the highest extraction efficiency was obtained when the ingredients combined at the ratios of Example 1 and Example 2 in Table 1 below were used as an extraction solvent.

TABLE 1

| Classi-fication | Ingredient | Example 1 | Example 2 | Comparative Example 1 | Comparative Example 2 |
|---|---|---|---|---|---|
| 1 | Purified water | Balance | Balance | 100 (hot water) | — |
| 2 | Ethanol | — | — | — | 100 |
| 3 | Glycerin | 15 | 15 | — | — |
| 4 | 1,3-butylene glycol | 20 | 20 | — | — |
| 5 | 1,3-propanediol | 10 | — | — | — |
| 6 | 1,2-hexanediol | 1 | 1 | — | — |
| 7 | Ethylhexyl glycerin | 0.1 | 0.1 | — | — |
|  | Total weight | 100 | 100 | 100 | 100 |

(The Unit of the Values in Table 1 is % by Weight)

The extraction efficiencies of Example 1, Example 2, Comparative Example 1 and Comparative Example 2 for EGCG were as shown in Table 2 below.

TABLE 2

| Extraction solvent | Extraction efficiency | Remarks |
|---|---|---|
| Hot water (Comparative Example 1) | 66% | The calculation is based on the extracted amount (42 mg) of EGCG in the case of using Example 1 for 1 g of green tea (that is, when the amount of the whole extract is 100 g) |
| Ethanol (Comparative Example 2) | 82% | |
| Example 1 | 100% | |
| Example 2 | 94% | |

Here, EGCG is only one of the index materials that can be easily analyzed among the various active ingredients extracted. Thus, the results do not mean that the extraction efficiency according to Examples, etc. is high only for EGCG. It can be seen that the extraction efficiency of Examples, etc. according to one aspect of the present invention is high for any ingredient that can be extracted from green tea or fermented green tea.

The extraction solvent of Examples is a combination of materials that can be used as cosmetics. The extraction solvent itself can be used as a skin cosmetic solution (cosmetics), etc. Also, it was found that unlike organic solvents such as ethanol, ethyl acetate and hexane, the extraction solvent of Examples can be directly used as cosmetics without solvent removal or additional processing, because it does not irritate the skin and thus is safe for the skin. It can be seen that Example 1 and Example 2 are remarkably superior in terms of usability compared with Comparative Examples which use conventional solvents, because the extracted extract can be directly applied to the skin without additional processing. Also, when Example 1 and Example 2 are used, the useful ingredients of the raw material can be extracted more effectively, and the processing time is also minimized. Thus, it can be understood that the extracted ingredients are significantly better preserved by Example 1 and Example 2 than Comparative Examples, which use conventional solvents.

Test Example 1

Confirmation of Efficacy of Extract

Green tea extracts were prepared using the skin cosmetic solutions (solvents) of Example 1 and Example 2 according to Examples and applied to the skin to evaluate the efficacy. Specifically, the efficacy was evaluated under the conditions shown in Table 3 below. The results are shown in FIG. 1 to FIG. 5.

TABLE 3

| | |
|---|---|
| Test subjects | Women aged 39 to 49 (average age of 45.7) |
| Test period | 4 weeks |
| Test sites | face, forearm |
| Test items | Skin texture, moisture, elasticity, transparency, level of antioxidation |
| Time point of measurement | Measured and evaluated immediately after use of the product and after 1 week, 2 weeks, and 4 weeks from the use |

The skin texture was measured using a three-dimensional imaging device. Specifically, it was measured using PRIMOS® premium (GFMesstechnik GmbH, Germany). Images of the same site were taken at each time point of measurement and compared. The analysis was performed using a roughness parameter or a wrinkle analysis parameter.

The skin moisture was determined through a skin moisture measurement using capacitance. Moisture content of the cheek area was measured three times at each time point using Corneometer® CM 825 (C+K, Germany) and the mean value was analyzed.

The skin elasticity was measured by a suction method using Cutometer® MPA580 (C+K Germany). The skin elasticity was analyzed after performing suction 3 times by turning on and off the negative pressure of 450 mbar at an interval of 2.0 seconds.

The skin transparency was measured using diffuse reflection. The diffuse reflection value of the cheek skin area was measured at the angle of 60° using Radioscan™ (True system, Korea).

The level of antioxidation of the skin was determined by measuring the antioxidant index (catalase activity) of skin keratin. The keratin of the forearm was collected using D-squame disc® (Cuderm, USA) and a light absorption analysis was performed at 850 nm using SquameScan® 850 (Wetzlar, Germany) to quantify the amount of protein. Then, the catalase activity of the keratin was measured and analyzed using Catalase Activity Colorimetric/Fluorometric Assay kit (biovision, Inc., USA).

The results showed that the extracts obtained by Examples of the present invention have a high extraction efficiency. Also, it was found that the various extracted ingredients can be effectively preserved, because additional processing such as solvent removal is not necessary as the extracts were extracted with ingredients that can be directly used as a skin cosmetic solution. It was also found that when the extracts are directly applied to the skin, they exert remarkable effects on skin texture, skin moisture, skin elasticity, skin transparency and the level of antioxidation of the skin (FIG. 1 to FIG. 5).

Test Example 2

Comparison of Cytotoxicity Between the Extracts According to Examples and Comparative Examples The cytotoxicity was evaluated using the Cell Proliferation & Toxicity Assay (CCk-8). Specifically, HEKn cells were seeded in a 48-well plate at a concentration of $1.2 \times 10^4$ cells/200 µL, cultured for 24 hours, treated with each sample (extracts obtained by using Examples and Comparative Examples) with a predetermined concentration. After 24 hours, the medium was replaced with a culture medium containing 8% of CCK-8 solution (Dojindo #CK04), followed by another culture at 37° C. for 2 to 3 hours. Finally, the absorbance was measured at 450 nm and the cell proliferation or cytotoxicity was calculated by comparing the result with the control ("CON").

Figure 1:
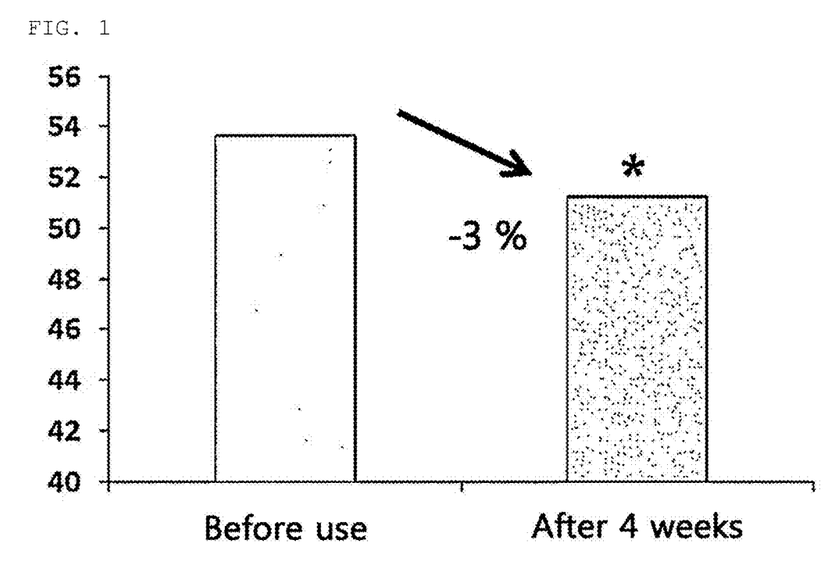
FIG. 1 shows the reduction of skin roughness when an extract extracted according to one aspect of the present invention is used.
Figure 2:
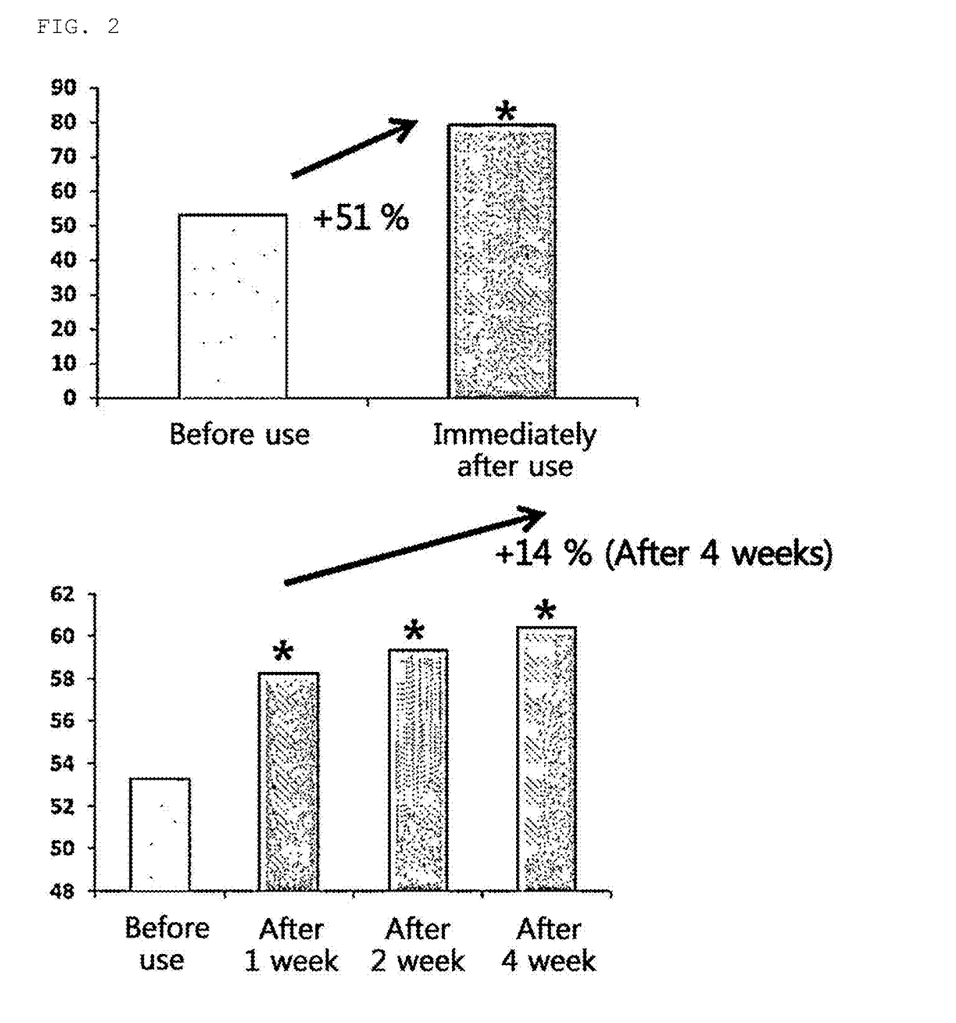
FIG. 2 shows the improvement of skin moisturizing effects when an extract extracted according to one aspect of the present invention is used.
Figure 3:
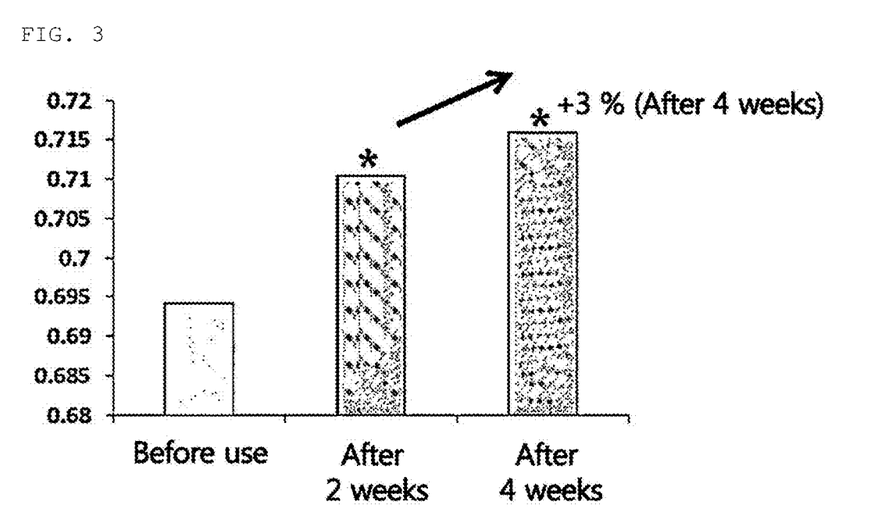
FIG. 3 shows the enhancement of skin elasticity when an extract extracted according to one aspect of the present invention is used.
Figure 4:
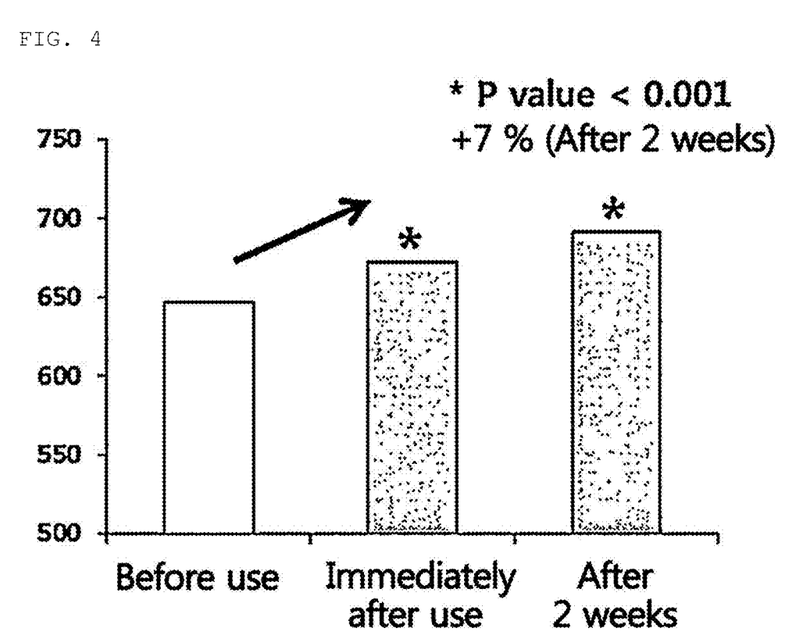
FIG. 4 shows the improvement of skin transparency when an extract extracted according to one aspect of the present invention is used.
Figure 5:
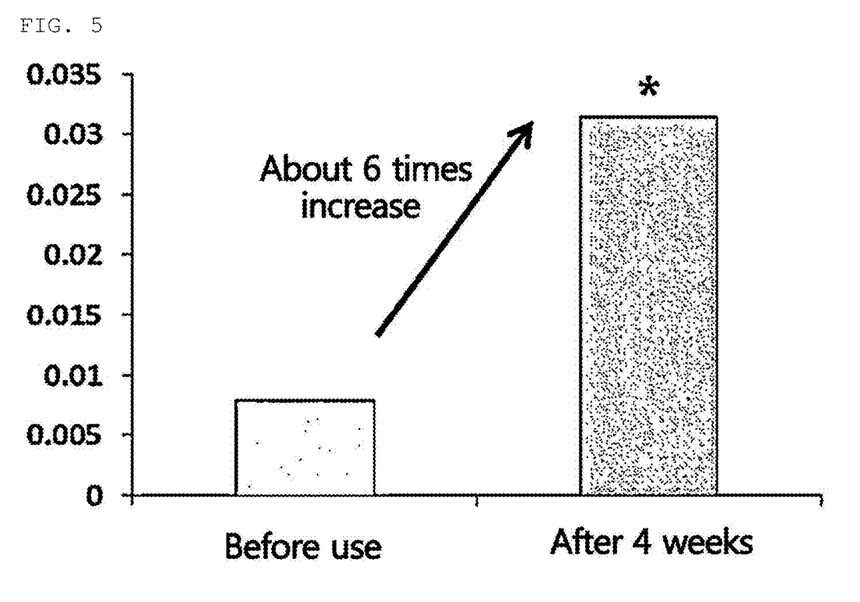
FIG. 5 shows that the use of an extract extracted according to one aspect of the present invention enhances the activity of antioxidant enzymes (catalase) in skin keratin, resulting in antioxidant effects on the skin.
Figure 6:
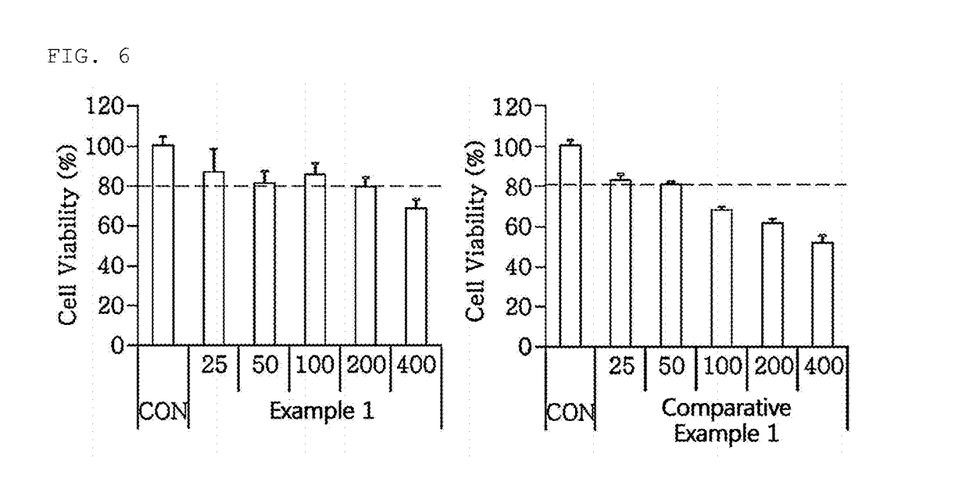
FIG. 6 shows the comparison results of the cytotoxicity of the extracts extracted using the skin cosmetic solution (solvents) of each of Example 1 according to one aspect of the present invention and Comparative Example 1.

The extracts (25, 50, 100, 200, and 400 ppm by weight) obtained by using Example 1 and Example 2 were found to be safer in terms of cytotoxicity than the extracts obtained by using Comparative Example 1 ("CON" in FIG. 6 represents a group not treated with an extract).

Test Example 3

Comparison of Anti-Inflammatory Effects, Antioxidant Effects and Anti-Aging Effects of the Extracts of Examples and Comparative Examples The anti-inflammatory effects, antioxidant effects and anti-aging effects were compared between the extracts of Examples and Comparative Examples.

Specifically, the expression of IL-1α (interleukin-1 alpha), COX2 (cytochrome c oxidase subunit 2), DCF-DA (dichlorofluorescin diacetate), NF-E2-related factor-2 (Nrf2), Keap-1 (Kelch-like ECH associated protein 1), etc. was evaluated by quantitative PCR, including RNA extraction and PCR analysis. $2 \times 10^5$ HEKn cells were seeded in a 6-well plate and cultured for 24 hours. The cells were treated with each sample (extracts obtained by using Examples and Comparative Examples) of a predetermined concentration. After 24 hours, cell lysis was performed with Trizol and RNA was isolated. After quantifying RNA, cDNA was synthesized. Then, each gene was subjected to real time PCR using a Taqman probe. RPLP0 gene was used as the internal control gene. Finally, the relative gene expression values were quantified using Ct values (a fine dust sample was used as the irritant to induce inflammation and sodium ascorbate was used as the positive control for DCF-DA).

The anti-aging was evaluated by MMP-1 (Matrix Metalloprotease-1) ELISA. Hs68 cells were seeded in a 24-well plate at a concentration of $3.6 \times 10^4$ cells/600 µL and cultured for 24 hours. After replacing the medium with a serum-free medium, the cells were cultured for another 4 hours and then stimulated with UVB at 35 mJ/cm$^2$. The cells were then treated with two types of samples (extracts obtained by using Examples and Comparative Examples) and the positive control (retinoic acid (RA), which is a representative MMP-1 expression inhibitor) of each concentration. After 48 hours from the treatment with the samples, the culture solutions were collected and the amount of MMp-1 was measured by ELISA.

Figure 7:
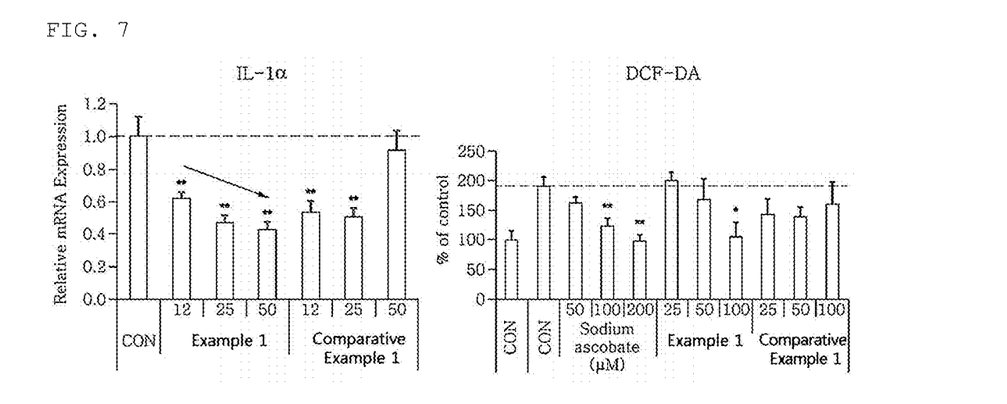
FIG. 7 shows the measurement results of the degree of expression of IL-1α and DCF-DA when using the extracts extracted using the skin cosmetic solution (solvent) of each of Example 1 according to one aspect of the present invention and Comparative Example 1.

The extracts obtained by using Example 1 and Example 2 were found to decrease the expression of IL-1α and DCF-DA in a concentration-dependent manner. In particular, the expression of IL-1α and DCF-DA was much lower than in the extracts obtained by using Comparative Examples, which use conventional solvents. Thus, the extracts obtained by using Example 1 and Example 2 were found to be much more effective in anti-inflammatory and antioxidant effects than the extracts obtained by using a conventional solvent (see FIG. 7; the "CON" in the left drawing of FIG. 7 represents a control group which was treated with an irritant to induce inflammation and not treated with an extract of Examples or Comparative Examples; the left "CON" in the right drawing of FIG. 7 represents a group subjected to no treatment; the right "CON" in the right drawing of FIG. 7 represents a group treated with ultraviolet ray only; and the unit of the X-axis is µM).

Figure 8:
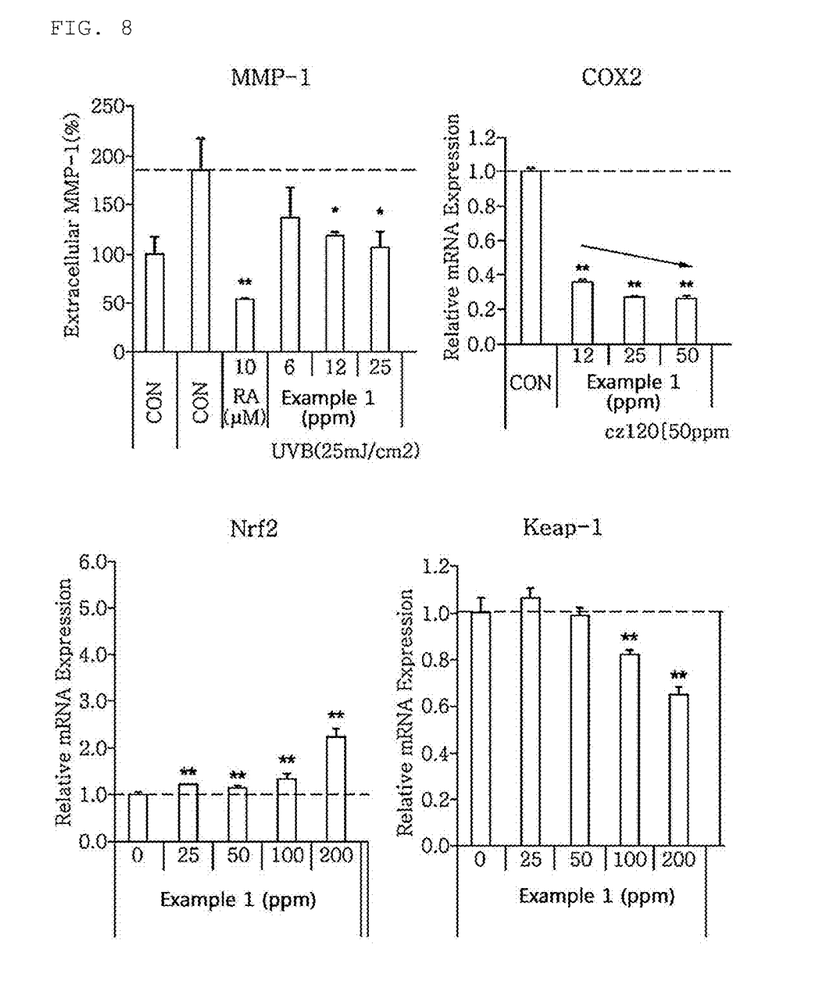
FIG. 8 shows the evaluation results of MMP-1, COX2, Nrf2 and Keap-1 when using the extracts extracted using the skin cosmetic solution (solvent) of Example according to one aspect of the present invention.

Also, the extracts obtained by using Example 1 and Example 2 were found to decrease the MMP-1 concentration and COX2 expression, increase the Nrf2 expression, and decrease the Keap-1 expression in a concentration-dependent manner (Keap1 protein is decomposed under oxidative stress conditions to stabilize Nrf2 and the Nrf2 enters the nucleus and acts as a transcription factor to increase the expression of antioxidant genes such as NQO1, HO-1 and GCLC) and thus have excellent anti-aging, anti-inflammatory and antioxidant effects (see FIG. 8; the first "CON" in the upper left drawing represents a group subjected to no treatment; the second "CON" in the upper left drawing represents a group treated with ultraviolet ray only; the "CON" in the upper right drawing represents a group not treated with an extract obtained by using Examples or Comparative Examples; the ppm in the drawings means ppm by weight; and "cz120" is the name of the fine dust sample to induce inflammation in the COX2 expression test).

Formulation Example 1

Nourishing Lotion

1% by weight of fermented green tea was extracted using Example 1 according to one aspect of the present invention. A proper amount of fragrance and 5% by weight (based on the total weight of the extract) of squalane were added to the resultant extract to prepare a nourishing lotion.

Formulation Example 2

Softening Lotion

5% by weight of fermented green tea was extracted using Example 1 according to one aspect of the present invention. A proper amount of fragrance, 0.5% by weight (based on the total weight of the extract) of liquid paraffin, 5% by weight of caprylic/capric triglyceride, 1.5% by weight of polysorbate 60, 5% by weight of squalane, and 4% by weight of beeswax were added to the resultant extract to prepare a softening lotion.

Formulation Example 3

Pack

3% by weight of fermented green tea was extracted using Example 1 according to one aspect of the present invention. 0.3% by weight (based on the total weight of the extract) of PEG 12 nonylphenyl ether, 0.1% by weight of allantoin, 13% by weight of polyvinyl alcohol were added to the resultant extract, and the thus obtained product was applied to the surface of a pack to prepare a pack.

The preparing method according to one aspect of the present invention achieves a much higher process efficiency than the methods using a conventional solvent. Also, a cosmetic composition prepared with an extract obtained by using an extraction solvent according to one aspect of the present invention has a high amount of the extracted active ingredient and exhibits remarkably excellent effects on the skin.

While the present invention has been described with respect to the specific embodiments, it will be apparent to those skilled in the art that various changes and modifications may be made without departing from the spirit and scope of the invention as defined in the following claims.

The invention claimed is:

1. A cosmetic composition consisting of extraction solvent and an ingredient extracted thereby from a plant, wherein the extraction solvent is a skin cosmetic solution and the plant is a tea leaf,
wherein the skin cosmetic solution comprises
two or more selected from the group consisting of butylene glycol, propanediol, and hexanediol;
glycerin; and
a glycerin derivative,
wherein a content of the butylene glycol is 10 to 25% by weight based on the total weight of the skin cosmetic solution;
a content of the propanediol is 1 to 20% by weight based on the total weight of the skin cosmetic solution; or
a content of the hexanediol is 0.1 to 5% by weight based on the total weight of the skin cosmetic solution,
wherein a content of the glycerin is 5 to 20% by weight based on the total weight of the skin cosmetic solution; or
a content of the glycerin derivative is 0.01 to 10% by weight based on the total weight of the skin cosmetic solution.

2. The cosmetic composition according to claim 1, wherein the butylene glycol is 1,3-butylene glycol, the propanediol is 1,3-propanediol, and the hexanediol is 1,2-hexanediol.

3. The cosmetic composition according to claim 1, wherein the glycerin derivative is ethylhexyl glycerin.

4. The cosmetic composition according to claim 1, wherein the skin cosmetic solution comprises glycerin, butylene glycol, propanediol, hexanediol, and ethylhexyl glycerin.

5. The cosmetic composition according to claim 1, wherein
the weight ratio of the glycerin: the butylene glycol is 1:0.5 to 5;
the weight ratio of the butylene glycol: the propanediol is 1:0.04 to 2;
the weight ratio of the propanediol: the hexanediol is 1:0.005 to 5; or
the weight ratio of the hexanediol: the glycerin derivative is 1:0.002 to 100.

6. The cosmetic composition according to claim 1, wherein a content of epigallocatechin gallate in the extract is 20 to 60 mg relative to 100 g of the cosmetic composition.

7. A method of manufacturing the cosmetic composition according to claim 1, comprising the step of preparing an extract of a tea leaf using a skin cosmetic solution as an extract solvent to produce the cosmetic composition,
wherein the cosmetic composition consists of the extract of the tea leaf.

8. The method according to claim 7, wherein the plant is a fermented tea leaf.

9. The method according to claim 7, wherein the extraction is ultrasonic extraction, room temperature extraction, cold extraction, or reflux cooling extraction.

10. The method according to claim 7, wherein the extraction is performed at 10 to 50° C.

11. The method according to claim 7, wherein the extraction is performed for 3 to 30 hours.

12. The method according to claim 7, wherein the extraction is performed at 5 to 100 rpm.

13. The method according to claim 7, wherein the step of preparing the extract further comprises a filtering step.

14. The method according to claim 7, wherein the method further comprises the step of preparing a skin cosmetic solution before the step of preparing the extract.

* * * * *